(12) United States Patent
Schulz et al.

(10) Patent No.: US 8,747,406 B2
(45) Date of Patent: Jun. 10, 2014

(54) INSTRUMENTS FOR OSTEOLYSIS REPAIR

(75) Inventors: Olaf Schulz, Lakeland, TN (US); Kelly Schlachter, Bartlett, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 2105 days.

(21) Appl. No.: 11/353,313

(22) Filed: Feb. 14, 2006

(65) Prior Publication Data

US 2006/0190000 A1 Aug. 24, 2006

Related U.S. Application Data

(60) Provisional application No. 60/654,696, filed on Feb. 21, 2005.

(51) Int. Cl.
*A61F 2/46* (2006.01)

(52) U.S. Cl.
USPC ............................................. 606/86 R; 606/89

(58) Field of Classification Search
USPC .................................. 606/86 R, 89
See application file for complete search history.

(56) References Cited

U.S. PATENT DOCUMENTS

| | | | | |
|---|---|---|---|---|
| 2,139,361 A | * | 12/1938 | Fredrickson | 4/295 |
| 2,194,940 A | * | 3/1940 | Hiertz | 4/295 |
| 2,362,250 A | * | 11/1944 | Durst | 4/293 |
| 2,746,632 A | * | 5/1956 | Bramming | 215/270 |
| 3,606,073 A | * | 9/1971 | Burke | 220/288 |
| 3,805,776 A | * | 4/1974 | Thiele | 606/60 |
| 4,111,326 A | * | 9/1978 | Percarpio | 215/247 |
| 4,276,659 A | * | 7/1981 | Hardinge | 606/95 |
| 4,302,855 A | * | 12/1981 | Swanson | 606/95 |
| 4,450,591 A | * | 5/1984 | Rappaport | 128/898 |
| 4,744,110 A | * | 5/1988 | Ippoliti | 4/295 |
| 4,794,654 A | * | 1/1989 | Diethelm | 4/295 |
| 4,991,104 A | * | 2/1991 | Miller | 700/197 |
| 5,468,245 A | | 11/1995 | Vargas, III | |
| 5,573,529 A | * | 11/1996 | Haak et al. | 606/1 |
| 6,032,515 A | * | 3/2000 | Huber | 73/49.1 |
| 6,082,410 A | * | 7/2000 | Pohar | 138/89 |
| 6,251,141 B1 | * | 6/2001 | Pierson et al. | 623/23.48 |

(Continued)

FOREIGN PATENT DOCUMENTS

| | | |
|---|---|---|
| EP | 0143847 A1 | 6/1985 |
| EP | 0 143 847 A1 * | 12/1985 |

OTHER PUBLICATIONS

Vittorio Iaccarino, Percutaneous intralesional brushing of cystic lesions of bone: a technical improvement of diagnostic cytology, 1990, International Skeletal Society, 19:187-190.*

(Continued)

*Primary Examiner* — Ellen C Hammond
(74) *Attorney, Agent, or Firm* — Duane Morris LLP

(57) ABSTRACT

A plug for plugging a hole of a bone or implant body during injection of an osteoregenerative material comprising, generally, a plug body, the plug body configured to plug a hole of the body to prevent osteoregenerative material from leaking through the hole, and a tail, the tail attached to the plug body for use in removing the plug body from the hole. In one embodiment, the plug body has an insertion cavity on a trailing end thereof for use in inserting the plug into a hole of the body. The plug body preferably has a frustoconical configuration. The plug body is preferably made of a resilient material, such as silicon.

21 Claims, 14 Drawing Sheets

(56) References Cited

U.S. PATENT DOCUMENTS

| | | | |
|---|---|---|---|
| 6,629,984 B1 * | 10/2003 | Chan | 606/148 |
| 7,399,742 B2 * | 7/2008 | DiMauro et al. | 514/2 |
| 2004/0236424 A1 * | 11/2004 | Berez et al. | 623/14.12 |

OTHER PUBLICATIONS

International Search Report, PCT International Search Report mailed Jun. 27, 2006 for PCT/US2006/005612 (filed Feb. 17, 2006).

* cited by examiner

FIG. 1C     FIG. 1B     FIG. 1D

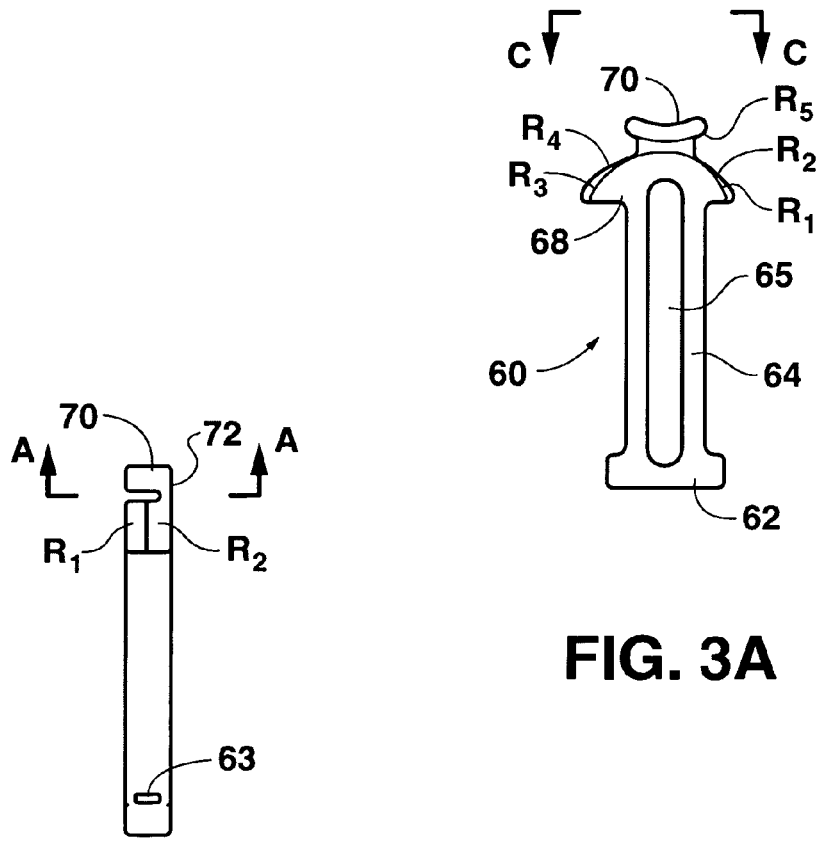
FIG. 3A
FIG. 3B
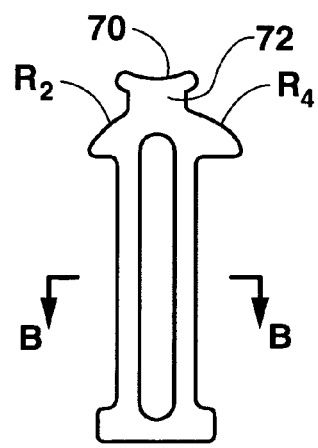
FIG. 3C

INSTRUMENTS FOR OSTEOLYSIS REPAIR

CROSS REFERENCE TO RELATED APPLICATIONS

This application claims priority to and incorporates by reference U.S. Provisional Patent Application Ser. No. 60/654,696, filed Feb. 21, 2005, which is pending.

FIELD OF THE INVENTION

The present invention relates to bone repair, and more particularly to repair of bone afflicted with osteolysis and other degenerative bone conditions.

BACKGROUND OF THE INVENTION

Osteolysis is a medical condition involving dissolution of bone. Unfortunately, osteolysis often occurs in the bone adjacent to an orthopedic implant, such as a hip or knee implant. Osteolysis forms osteolytic lesions or voids in the bone. Osteolytic lesions are typically soft and spongy, and are unsupportive of orthopedic implants. An osteolytic lesion can cause a well-fixed implant to loosen. To treat osteolysis in the area of an implant, it is often necessary to conduct a revision surgery in which the old implant is removed, the lesion is cleaned out by debriding the local area, and then a larger revision implant is put in. To gain fixation, the revision implant requires substantial hardware to compensate for the significant bone loss.

Osteolytic lesions can occur in many other parts of the body where implants have been implanted, e.g. humerus, tibial plateau, distal femur, and acetabulum. Accordingly, the need to treat osteolytic bone lesions after joint replacement surgery is a widespread problem.

OBJECTS AND SUMMARY OF THE INVENTION

It is an object of the invention to provide an improved treatment of osteolytic bone lesions.

It is another object of the invention to provide an improved debridement of osteolytic bone lesions that does not require removal of a previous implant.

It is an object of the invention to avoid or delay revision surgery by debriding osteolytic bone lesions and regenerating bone in the lesions.

It is an object of the invention to conserve bone by preserving and regenerating bone in osteolytic lesions.

In order to achieve the foregoing and other objectives and advantages of the invention, a plug for plugging a hole of a bone or implant body during injection of an osteoregenerative material is provided comprising, generally, a plug body, the plug body configured to plug a hole of the body to prevent osteoregenerative material from leaking through the hole, and a tail, the tail attached to the plug body for use in removing the plug body from the hole. The tail is preferably formed from a cord. A portion of the cord is preferably embedded in the plug body. A portion of the cord preferably traverses the plug body from a leading end to a trailing end of the plug body. A knot is preferably formed in the portion of the cord that is embedded in the plug body. The plug can be provided with a second tail, with the second tail being attached to the plug body for use in removing the plug body from the hole. The tails are preferably formed from a single cord, with a portion of the cord passing through the body of the plug.

In one preferred embodiment, the plug body has an insertion cavity on a trailing end thereof for use in inserting the plug into a hole of the body. The plug body preferably has a frustoconical configuration, and preferably has a shoulder on a trailing end. The plug body is preferably made of a resilient material. The resilient material is preferably silicon, and is more preferably an implant grade silicon.

A method of repairing an osteolytic lesion associated with an implant is provided comprising plugging holes of the implant with one or more removable plugs prior to injecting a bone regenerative material into the lesion, such that the plugs prevent the bone regenerative material from leaking through the holes. The plugs can be provided with tails, and the tails can be used to remove the plugs from the implant.

A kit can be provided for treating osteolysis and other degenerative bone conditions. In a preferred embodiment, the kit includes at least one plug, a means for removing the plug from a hole, and a bone regenerative material. The kit preferably includes an osteolysis brush configured for use in debriding osteolytic material, as well as a multi-radius bender. The kit also preferably includes one or more of a curette, a cannula configured for use in suctioning osteolytic material out of the osteolytic lesion, a syringe for injecting osteoconductive material into the osteolytic lesion, a syringe loader for transferring the osteoconductive material to the syringe, and a syringe needle.

Methods of debriding osteolytic material from an osteolytic lesion in the vicinity of an acetabular shell implant are provided. One preferred method comprises inserting a curette through at least one hole of the acetabular shell in order to gain access to the osteolytic lesion located behind the shell, and manipulating the curette through the hole to thereby scrape osteolytic material from the lesion. The curette can be bent in order to reach areas of the osteolytic lesion. Additional osteolytic material can be removed by inserting a brush through at least one of the holes of the acetabular shell and manipulating the brush to entrap and remove residual particles of osteolytic material from the osteolytic lesion. Loose osteolytic material can be removed by inserting a cannula through at least one of the holes of the acetabular shell and suctioning the osteolytic material through the cannula. Osteoregenerative material can then be injected behind the shell in order to fill the lesion and regenerate bone. In order to prevent osteoregenerative material from seeping through the holes, the holes of the implant can be plugged prior to injecting the osteoregenerative material behind the shell. A cannula can be inserted through a plug body and osteoregenerative material can be injected through the plug.

The foregoing and other objects, features, aspects and advantages of the invention will become more apparent from the following detailed description of the invention when considered in conjunction with the accompanying drawings.

BRIEF DESCRIPTION OF THE DRAWINGS

FIGS. 1A-1I provide views of preferred embodiments of plugs for use in osteolysis repair.

FIGS. 3A-3H provide views of one preferred embodiment of a multi-radius bender for use in osteolysis repair.

PREFERRED EMBODIMENTS OF THE INVENTION

Figure 1A:
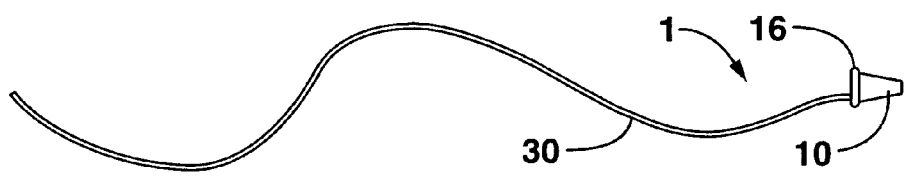

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

The present invention is directed to an osteolysis kit and the various individual components of the kit.

Plugs

As shown in FIGS. 1A-1I, one aspect of the invention is a removable plug 1. As will be described in further detail below, the plugs 1 are used to temporarily plug holes in an implant or bone while injecting an osteoregenerative material into an osteolytic void located behind or adjacent the implant or bone. The plug 1 will be discussed with reference to a hip revision procedure in which the osteolytic site is accessed through holes in an acetabular shell. However, it will be appreciated that the concepts disclosed herein can be used with any type of implant through which an osteolytic site can be accessed through holes in the implant (e.g. knee implants; shoulder implants), as well as through bone holes that communicate with an osteolytic lesion.

The body 10 of the plug 1 preferably has a frustoconical configuration having a conical side wall 14 tapering toward a flat bottom/distal wall 12. The conical side wall 14 is shaped such that a leading or distal portion of the side wall 14 has a diameter less than that of the shell holes, while a trailing or proximal portion of the side wall 14 has a diameter greater than that of the shell holes, such that a section of the side wall 14 serves to plug the shell hole. The conical side wall 14 allows a single size plug 1 to plug a plurality of sizes of shell holes, thus reducing inventory in an osteolysis kit. The side wall 14 could be provided with annular ribs (not shown) or other retaining structures. To prevent over-insertion of the plug body 10, the plug body is preferably provided with a shoulder 16 extending along the rim 15 of the plug body 10.

Figure 1E:
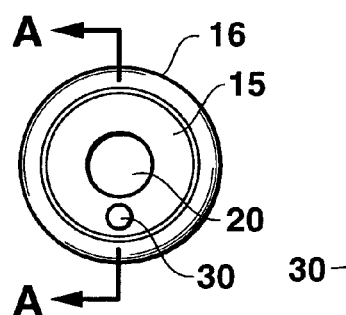
Figure 1E:
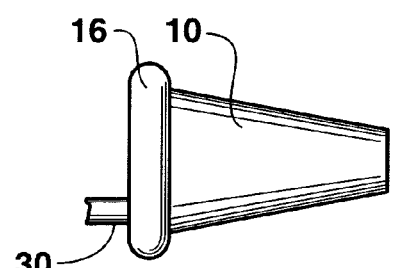
Figure 1E:
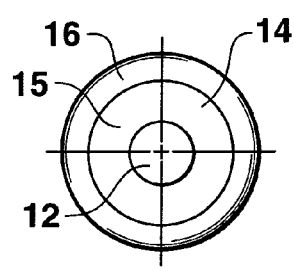
Figure 1E:
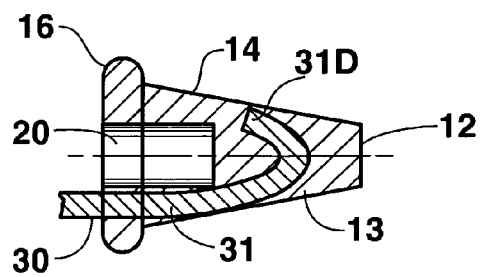
Figure 1F:
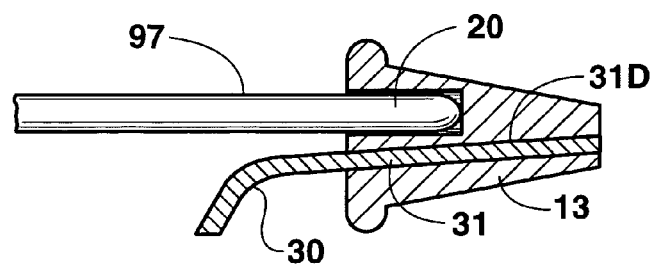

As shown in the top view of FIG. 1C and the cross-section view of FIG. 1E, the plug body 10 preferably has an insertion cavity 20 through a trailing end of the plug body 10. The insertion cavity 20 is preferably a bore and is used to insert the plug body 10 into the hole of a shell. As shown in FIGS. 1F and 4F, the tip of a blunt instrument or insertion tool 97 is inserted into the insertion cavity 20, and the instrument is then used to force the plug body 10 into a shell hole.

Figure 1G:
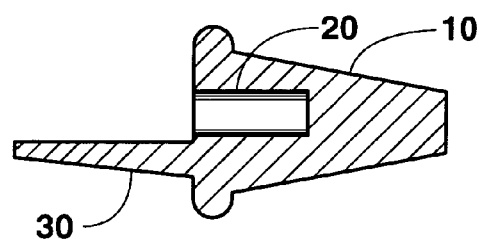

To assist in removing the plug body 10 from the hole, the plug body 10 is preferably provided with a tail 30. As shown in FIG. 1, the tail 30 is preferably formed as a portion of a cord 31. FIG. 1E provides details of a preferred embodiment of a connection between the plug body 10 and the tail 30. As shown in the cross-section view of FIG. 1E, a distal portion 31D of the cord 31 is embedded in a solid bottom portion 13 of the plug body 10. The tail 30 extends through the rim 15 of the plug body 10 and into the solid bottom portion 13. FIG. 1F provides details of an alternative preferred embodiment in which the tail 30 enters the plug body 10 through an area inside of the rim 15. As shown in FIG. 1F, the tail 30 may traverse the body 10 of the plug 1. As also shown in FIG. 1F, the tail 30 can pass through the axis or slightly off-axis of the plug body 10, in which case the insertion cavity 20 is formed adjacent to, rather than along, the axis of the plug body 10. The cross-section view of FIG. 1G shows an alternative preferred embodiment in which the tail 30 is integrally molded from the material that forms the plug body 10. The tail 30 of the embodiment of FIG. 1G has a short length, such as a stub that can be grabbed between the thumb and forefinger.

Figure 1H:
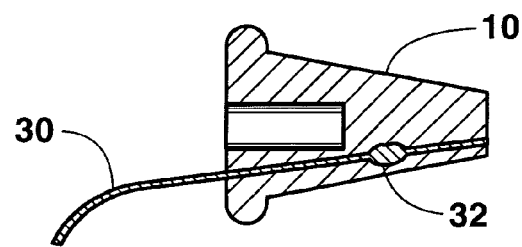
Figure 1I:
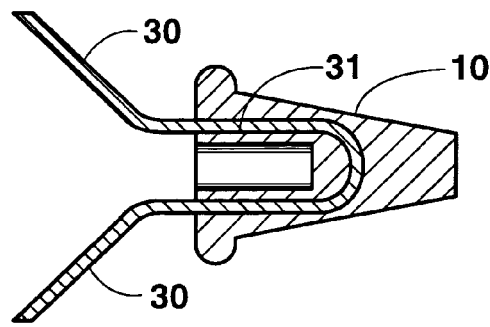

The cross-section view of FIG. 1H shows an alternative preferred embodiment in which a knot 32 is formed in a distal portion of the cord 31. The body 10 of the plug 1 is molded around the knot 32. The knot 32 assists in retaining the cord 31 in the plug 1. The cross-section view of FIG. 1I shows an alternative preferred embodiment in which the cord 31 loops through the body 10 of the plug 1, forming a pair of tails 30.

The plug 1 is made of a resilient material, such as a Shore A 55 durometer instrument or implant grade silicone or C-FLEX polymer. The tail 30 is preferably made of an implantable, braided polyester cord 31. In one manufacturing method, the plug 1 is formed with excess cord 30 extending from the bottom or distal wall 12 of the plug. The excess cord is then cut off such that the cord 30 does not extend beyond the bottom wall 12. The tail 30 is preferably of a length sufficient to allow a surgeon to securely grasp the tail 30 for use in removing the plug 1, such as by wrapping the tail 30 around a finger. The tail 30 is preferably between about 20 to 40 cm in length, and is preferably 30.5 cm in length. As mentioned above, much shorter tails can be used. A short tail may be preferable for plugs 1 in which the tail 30 is integrally molded from the same material that forms the plug body 10 (e.g. a silicon body 10 and tail 30).

Osteoregenerative materials that can be used with the plugs 1 include osteoconductive materials (e.g. calcium sulfate; calcium phosphates; hydroxyapatite) as well as osteoinductive materials (e.g. calcium sulfate plus demineralized bone matrix; autograft cancellous bone; allograft cancellous bone). The osteoregenerative material is preferably applied in an injectable form (e.g. MIIG® injectable bone paste, available from applicant Wright Medical Technology, Inc. of Arlington, Tenn.). Cancellous chips or pellet forms of osteoregenerative materials can also be used (e.g. OSTEOSET® bone graft substitute, available from applicant Wright Medical Technology, Inc.), since the plugs 1 will also serve to retain these materials.

Brush

Figure 2:
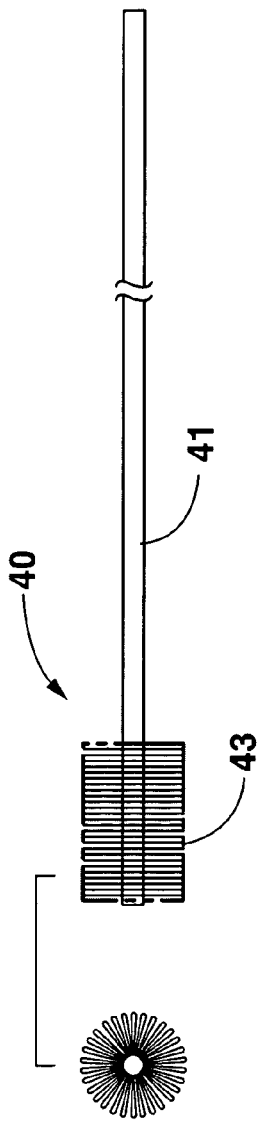
FIG. 2 provides a view of one preferred embodiment of an osteolysis brush for use in osteolysis repair.

To assist in removing osteolytic material from the osteolytic lesion, the osteolysis kit of the invention is preferably provided with a specially configured osteolysis brush. FIG. 2 shows a preferred embodiment of an osteolysis brush 40. The osteolysis brush 40 has a bristle portion 43 affixed to a lengthwise shaft 41. As indicated in FIG. 2B, the bristle portion 43 is configured to pass through an implant hole, such as through bristles radiated from the axis of the shaft 41 in a circumferential or twisted configuration. Viscous, gooey forms of osteolytic material become ensnared in the bristles 43, such that the brush 40 efficiently removes osteolytic material. The bristles 43 are preferably made of natural nylon grade 612 having a fiber size of about 0.25 mm. The shaft 41 is made of a strong but flexible material, such as interwoven steel wires, which allows the bristle portion 43 to be manipulated within the osteolytic lesion through an implant or bone hole, such as a shell hole. The shaft is preferably between about 20 to 30 cm long, and is preferably 25.4 cm long.

Ring Curette

Figure 4A:
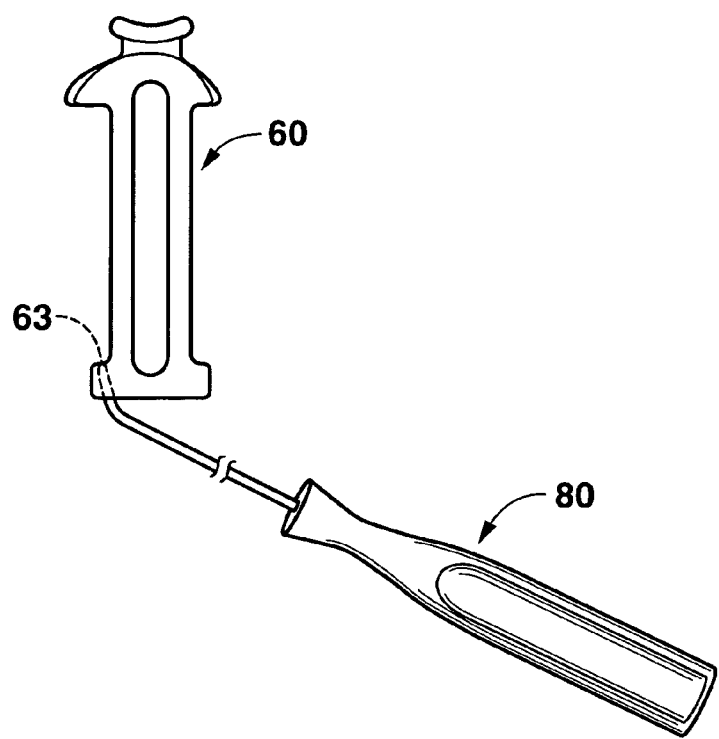
FIGS. 4A-4G show preferred methods of osteolysis repair using the instruments of the invention.

As shown in FIG. 4A, the osteolytic kit of the invention preferably includes a ring curette 80 having a ring tip 82 joined to a handle 88 by a connecting shaft 86. The ring tip 82 has an opening passing through the tip 82. The ring tip 82 provides an effective structure for scraping osteolytic material from the surface of the lesion. Ring curettes are known and are used for various medical procedures, but as far as the applicant has been able to determine, ring curettes have not previously been used to remove osteolytic material. Conventional ring curettes typically have straight shafts and the ring tip is joined to the shaft at a straight or fixed angle. Thus, ring curettes are generally rigid and difficult to bend. Since osteolytic lesions and their associated implants come in a multitude of shapes, it is often necessary to bend the curette in order to achieve a workable configuration for cleaning out the lesion. Curette manipulation is particularly necessary when attempting to navigate through an implant hole and behind the implant surface to scrape off the osteolytic material.

Multi-Radius Bender

To facilitate bending of curettes and cannulas, the osteolysis kit of the invention is preferably provided with a multi-radius bender 60 of the type shown in FIG. 3. The embodiment shown in FIG. 3 provides five set bending radiuses $R_1$-$R_5$. Additional or fewer radii could be provided, but it is believed that the embodiment shown in FIG. 3 provides an optimum balance between bending options, instrument size, and complexity. In the preferred embodiment shown in FIG. 3A, the bender 60 includes a base portion 62, a generally lengthwise body portion 64, and a bender portion 68. The body portion 64 may comprise a pair of parallel columns forming a lengthwise slot 65 in the bender 60. The body portion 64 and the slot 65 assist in handling the instrument. For example, a surgeon working with wet gloves can secure his or her fingers in the opening 65 while grasping one or both of the column portions 64. As indicated in FIG. 3A, the opening 65 can be provided with contoured edges, such as along upper and lower ends of the opening 64. Another advantage of the opening is that it reduces the amount of material used to manufacture the bender 60.

Figure 3D:
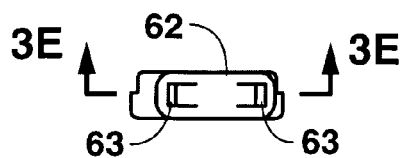
Figure 3E:
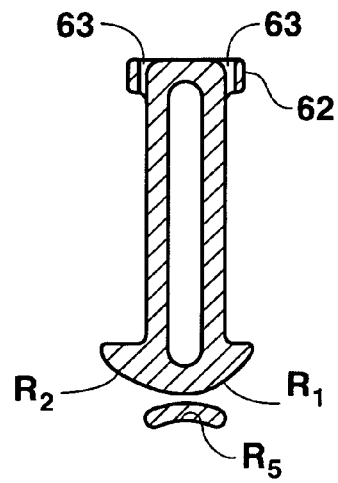
Figure 3F:
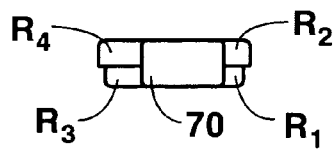
Figure 3G:
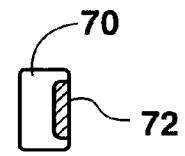
Figure 3H:
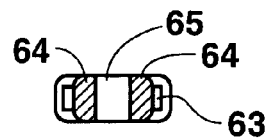
Figure 4B:
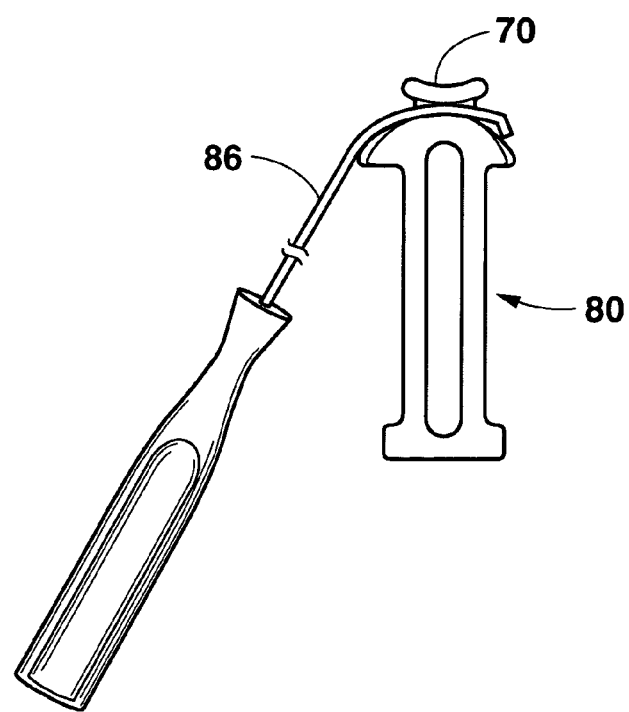

In the embodiment shown in FIG. 3A, a plurality of bending surfaces or bending radiuses R1-R4 are formed along an upper surface of the bender portion 68. Each of the radiuses R has a selected radius. However, as can be seen in FIG. 3A, pairs of radiuses are preferably formed along a shared bend, so as to reduce the dimensions of the instrument. For example, the cross-section view of FIG. 3E shows that radius $R_1$ and radius $R_2$ are formed along a common bend, yet have distinctly different radiuses. Radius $R_2$ has a longer radius, and consequently provides a more gentle curve than radius $R_1$. As can be seen in FIG. 4B, the shaft 86 of a curette or cannula is placed on a selected radius R and then bent along the radius R so as to achieve a shaft 86 curvature that generally matches that of the selected radius R. In FIG. 4B, the shaft 86 is being bent along bending radius $R_4$.

In order to retain the shaft 86 in position along the selected radius R during bending, the bender 60 is provided with a shaft holder 70. As indicated in FIGS. 3B and 4B, at least a portion of the holder 70 is spaced to closely receive a curette shaft 86 or cannula between the shaft holder 70 and the various bending radiuses R. As shown in FIG. 3b, the shaft holder 70 is attached to the bender portion 68 by a neck 72. The neck 72 can be configured for use in seating and retaining the shaft 86 along bending radiuses $R_2$ and $R_4$.

In order to provide yet another bending radius R, a lower surface of the shaft holder 70 is preferably curved into a bending radius $R_5$. Unlike the other radiuses R, the shaft holder bending radius $R_5$ is used by bending the curette or cannula upward, in a direction away from the base 62 of the bender 60.

To provide aggressive bending of instruments, the bender 60 is also preferably provided with at least one instrument tip bend aperture 63. In a preferred embodiment shown in FIG. 3, the instrument tip bend aperture 63 is formed through the base portion 62 of the bender 60, but the instrument tip bend aperture 63 can be formed at other locations on the bender 60.

As shown in FIG. 3E, the instrument tip bend aperture 63 preferably includes a curved portion for use in forming a smooth bend of the curette tip 82 or cannula. As further shown in FIG. 3E, the bender 60 is preferably provided with two instrument tip bend apertures 63. The instrument tip bend apertures 63 are preferably different sizes for use in accommodating different sized instrument tips 82. As shown in FIG. 4A, the instrument tip bend aperture 63 is used by placing a tip 82 of an instrument, such as a curette or cannula, into the aperture 63 and then bending the tip (or an adjoining portion of the curette shaft 86 or cannula) against the edge of the aperture 63. As indicated in FIG. 4A, different selected degrees of bend can be achieved, depending primarily on how far the instrument handle 88 is moved relative to the aperture 63. The step of bending the instrument tip 82 is preferably carried out prior to the step of bending the shaft 86, since a bent shaft 86 will make it more difficult to achieve a selected degree of bend in the tip 82 area.

The multi-radius bender 60 can be used to readily form more aggressive tip and shaft bends than could be obtained by bending the instrument 80 by hand. The uni-body construction of the multi-radius bender provides a durable structure that can be autoclaved and reused, or readily manufactured in a disposable embodiment. Further, through experience, a surgeon will develop familiarity with the set curvatures of the radiuses R, and thus will be able to readily attain consistent degrees of bending.

Use of Instruments

In operation, the osteolysis kit of the invention is used in a multi-part procedure for debridement of osteolytic material from bone lesions. Methods of using the osteolysis kit will be discussed with reference to a hip revision, but, as mentioned above, the methods can be used for osteolysis repair with other types of implants, such as knee and shoulder implants. The original cup liner is removed from the shell 200 using techniques known to those of skill in the art. The ring curette 80 can then be used to clean the lesion 100. As shown in FIG. 4A, a tip 82 of a ring curette 80 is placed in the tip bender 63. As shown in FIG. 4B, a distal portion of the shaft 86 of the curette 80 is then placed in a selected radius R of the bender 60. In FIG. 4B, the shaft 86 has been placed for bending along radius $R_4$. By pulling down on the handle 88 of the curette 80, the surgeon can readily bend a distal portion of the shaft 86 into a bend that substantially matches the radius of the selected radius R.

Figure 4C:
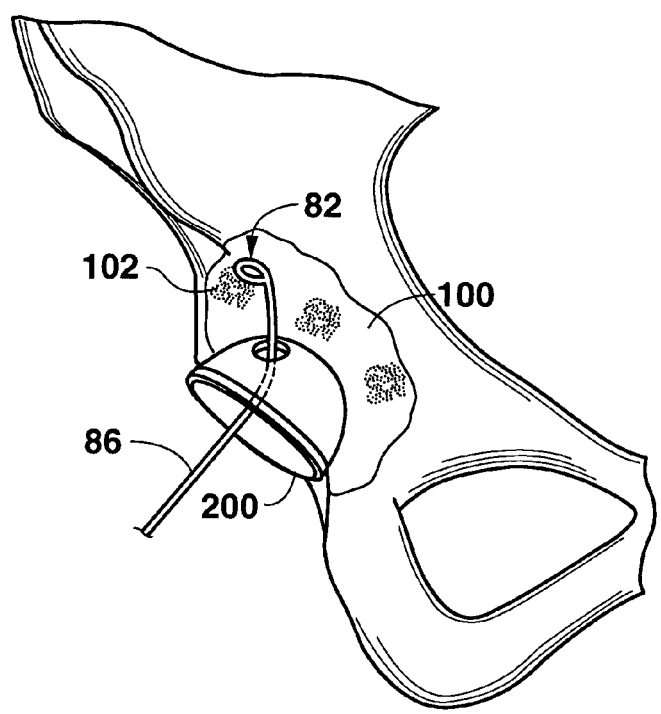

As shown in FIG. 4C, the shaft 86 of the curette 80 is inserted through a hole of the acetabular shell 200 in order to gain access to the osteolytic lesion 100 located behind the shell 200. The curette 80 is then manipulated to scrape osteolytic material 102 from the lesion 100. The osteolytic material 102 is shown in representative form in the drawings. Osteolytic material 102 typically coats the entire surface of the lesion 100. The open bore of the ring tip 82 of the curette 80 allows osteolytic material to readily pass through the tip 82 during scraping, which is believed to yield a more efficient scraping process. If the surgeon has difficulty accessing a particular area of the lesion 100, the surgeon has the option of removing the curette 80 from the lesion 100, bending a second curette 80 into a desired configuration in the manner described herein, and inserting the second curette 80 into the lesion 100 for scraping of osteolytic material 102. Straight curettes 80 can be used, but it is believed that bent curettes 80 will provide better results, since they can be configured to reach areas of the lesion 100 that would be difficult or impossible to reach with a straight curette 80.

Figure 4D:
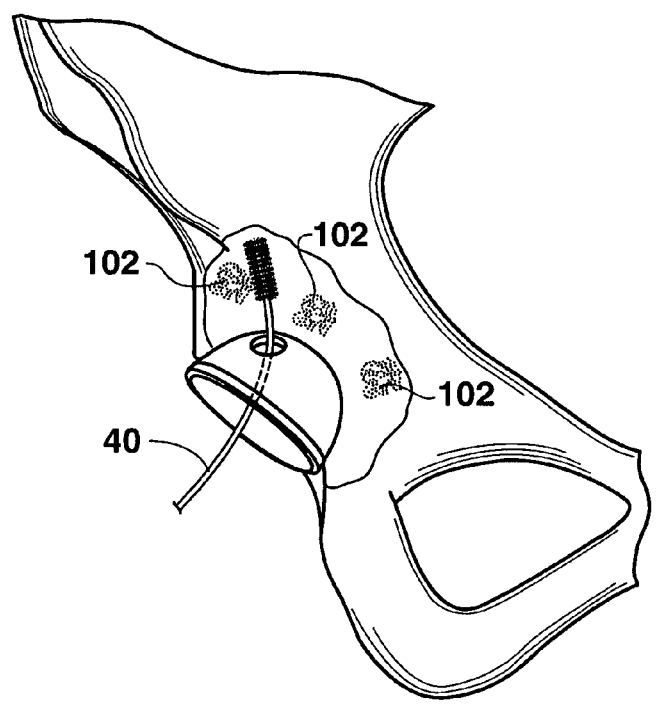

As shown in FIG. 4D, once osteolytic material 102 has been scraped from the lesion 100, the brush 40 can be inserted into the lesion 100 for use in brushing the wall of the lesion 100 to remove residual particles of osteolytic material 102. As indicated in FIG. 4D, the brush 40 not only cleans the walls, but is configured to entrap osteolytic material 102 in the bristles 43, such that the brush 40 can be used to remove osteolytic material 102.

Figure 4E:
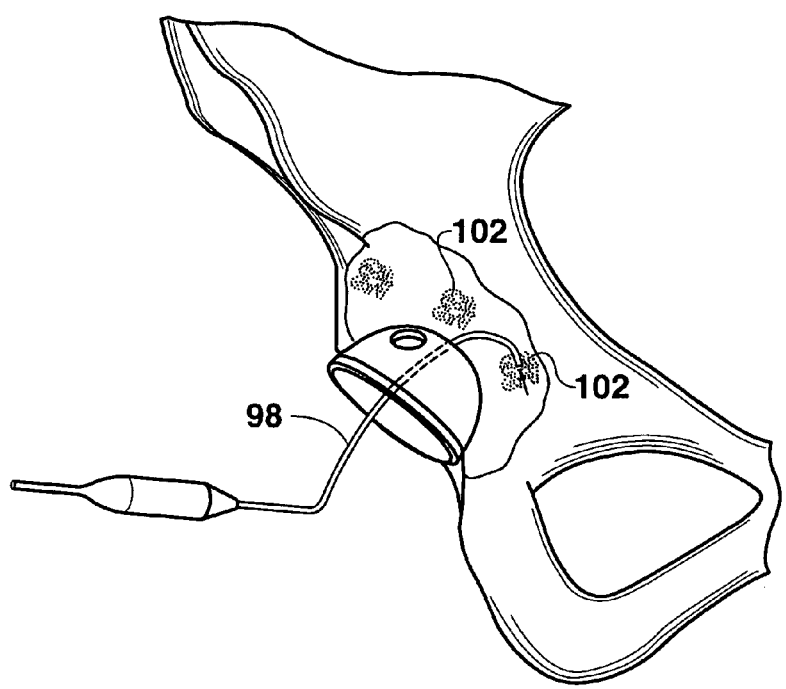
Figure 4F:
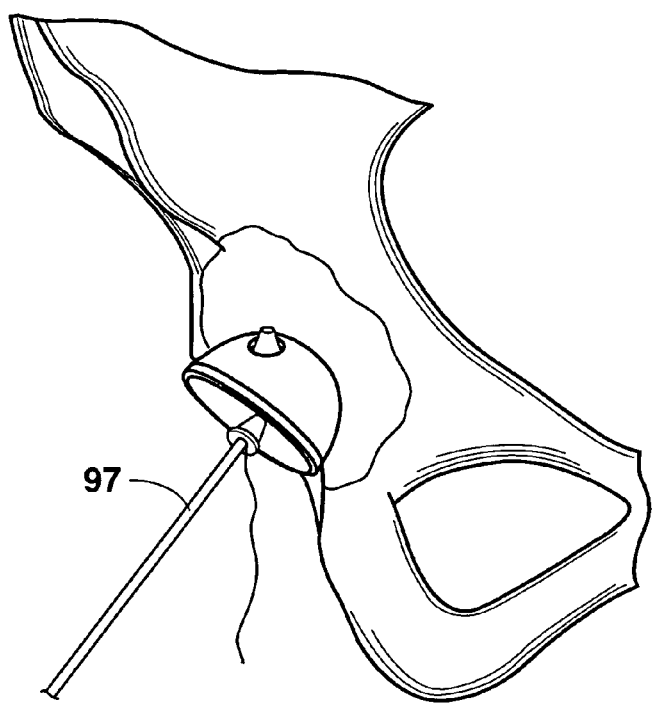

As shown in FIG. 4E, a metal cannula 98 is inserted into the lesion 100 and is used to suck out the loose osteolytic material 102. It may be necessary to bend the cannula 98, such as by using the bender 60, in order to access substantially all areas of the lesion 100. After suction of loose osteolytic material 102, it may be necessary to repeat some or all of the foregoing steps of scraping, brushing, and suction in order to insure that substantially all osteolytic material 102 has been removed from the lesion 100. Depending on the circumstances of the particular case, it may be preferable to carry out the cleaning steps in a different order, e.g. suction prior to brushing.

As shown in FIG. 4F, once a sufficient amount of osteolytic material 102 has been removed from the lesion 100, the plugs 1 are used to plug the holes in the implant 200 for use in applying an osteoregenerative material. In the embodiment shown in FIG. 4F, the implant 200 is an acetabular shell 200, and the holes are the holes that are used to secure the shell 200 to the hip bone, such as with bone screws. The plugs 1 can be inserted into the shell holes by hand. However, as shown in FIG. 4F, the plugs are preferably inserted by placing a blunt tip of an insertion instrument 97 into the plug's insertion cavity 20, and then manipulating the insertion instrument 97 to insert the plug 1 into a selected hole. The configuration of the plugs 1, including the resilient material from which they are made, allows the plugs 1 to be installed quickly and with little effort on the part of the surgeon. In a preferred embodiment, all but one of the shell holes are plugged, such that the open hole provides access to the osteolytic lesions. Alternatively, all of the holes can be plugged, in which case an injection cannula can be inserted through the body portion 10 of one of the plugs and the bone regenerative material can be injected through the plug body 10. In situations involving a small lesion 100, some of the implant holes may lie over normal bone, in which case plugs 1 are only used in the holes that overlay the lesion 100. Additionally, osteoregenerative material 310 may be applied to the lesion 100 other than through a hole of the implant, such as through a separate portal incision or by passing the injection cannula 301 around a side of the implant.

Figure 4G:
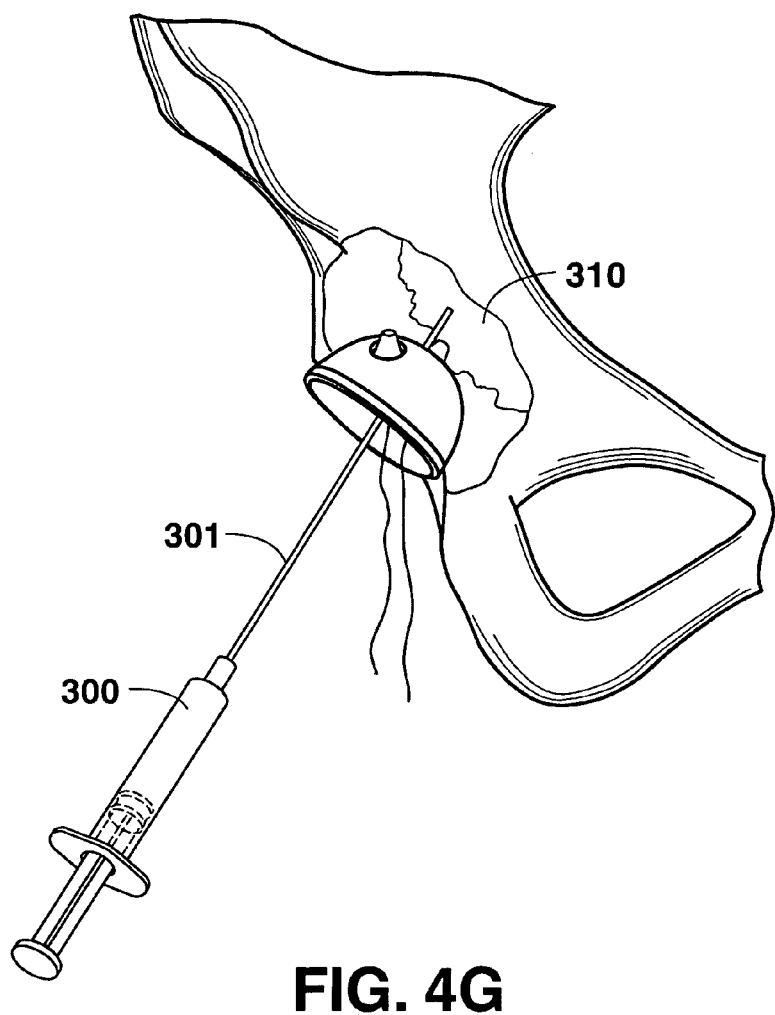
Figure 5:
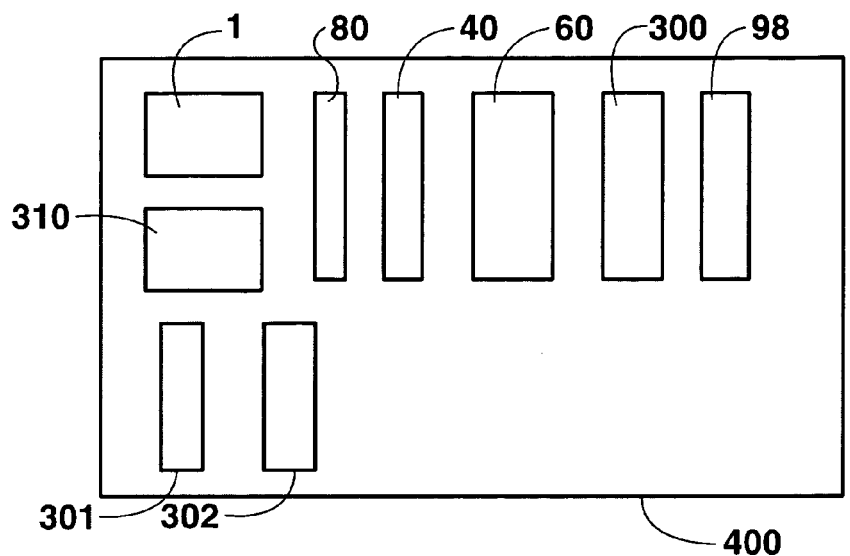
FIG. 5 shows a schematic view of instruments of a kit for osteolysis repair.

FIG. 4G shows the use of a syringe 300 and associated cannula 301 to inject an osteoregenerative material into the lesion 100. Because the shell holes are plugged with the plugs 1 of the invention, the osteoregenerative material cannot leak through the shell holes. Osteoregenerative material 310 is preferably inserted into the lesion 100 until the lesion 100 is substantially completely filled with osteoregenerative material 310. Because the shell holes are plugged, osteoregenerative material 310 typically will not start to leak out of the open shell hole until the void is full or substantially full, at which point excess material 310 is preferably forced through the open hole. Thus, the plugs 1 assist in determining when the void of the lesion 100 has been completely filled with osteoregenerative material 310. The plugs 1 are removed from the shell 200 simply by pulling on the tails 30, a procedure that takes only moments to perform. The plugs 1 can be removed at the discretion of the surgeon, such as when the void has been sufficiently filled or the osteoregenerative material has hardened sufficiently. Once the plugs 1 have been removed, the surgeon has completed the osteolysis repair and can proceed with subsequent stages of the revision procedure, including replacing the implant, which in the method shown in FIGS. 4A-4G would entail impacting a replacement cup liner into the shell 200.

As mentioned above, osteolytic conditions can occur with other types of implants. For example, in a knee implant, osteolysis can occur under the tibial base and along the stem of the tibial base. If the tibial base has fixation holes, it is possible to remove the polyethylene bearing surface, debride osteolytic material and inject osteoregenerative materials into the lesion through the holes using the methods described herein, and then insert a new polyethylene bearing surface into the tibial base. With implants that do not have holes, it will be possible in some circumstances to access the underlying lesion by working around the edge of the implant or through a hole in the bone. In such circumstances, it may be useful to plug bone holes with plugs 1 to assist with injection of osteoregenerative material.

In a preferred embodiment, the osteolysis kit of the invention includes a set of plugs 1, a means for debriding osteolytic material, and an osteoregenerative material 310. The osteoregenerative material is preferably an osteoconductive and/or osteogenic material. The kit preferably includes additional components, such as an osteolysis brush 40; a curette 80; a multi-radius bender 60; a blunt metal cannula 98 configured for use in suctioning osteolytic material out of the osteolytic lesion; a syringe 300 for injecting osteoconductive material into the osteolytic lesion; a syringe loader 302 for transferring the osteoconductive material to the syringe; and a syringe needle 301. The kit may also include instruments for removing the liner from the shell. All or part of the components of the kit are preferably disposable. The components of the kit are preferably arranged in a convenient format, such as in a surgical tray or case. However, the kit components do not have to be packaged or delivered together, provided that they are assembled or collected together in the operating room for use at the time of surgery.

A preferred bioresorbable material for use in the invention is an injectable form of calcium sulfate ($CaSO_4$). An acceptable injectable form of calcium sulfate is MIIG® injectable bone paste, which is sold by Wright Medical Technology, Inc. of Arlington, Tenn., the assignee of the present patent application. MIIG® injectable bone paste has superior compressive strength, is completely resorbable, regenerates bone, and is capable of passing through very small needles under manually applied pressure. While results will vary, the osteoconductive material may be resorbed and replaced by bone within twelve weeks. In preferred cases, use of the invention will halt or delay osteolysis.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A plug for plugging a hole of a bone or implant body during injection of an osteoregenerative material, comprising:
    a frustoconical plug body having a trailing end that tapers to an insertion end, said plug body configured to plug a hole of the body to thereby prevent osteoregenerative material from leaking through the hole, said plug body having an insertion cavity inwardly extending from the trailing end thereof in a direction that is parallel to a longitudinal direction of the plug and being sized and configured for use in inserting said plug into a hole of the body, the trailing end including a solid shoulder outwardly extending from the trailing end for preventing over insertion of the plug, and a tail attached to and extending from the trailing end of the plug body at a location adjacent to the insertion cavity, the tail being sized and configured for use in removing the plug body from the hole.

2. The plug of claim 1, wherein said tail is formed from a cord.

3. The plug of claim 2, wherein a portion of said cord is embedded in said plug body.

4. The plug of claim 3, wherein a portion of said cord traverses said plug body from a leading end to a trailing end of said plug body.

5. The plug of claim 3, further comprising a knot formed in said portion of said cord that is embedded in said plug body.

6. The plug of claim 3, wherein a portion of said cord traverses said plug body from a leading end to a trailing end of said plug body.

7. The plug of claim 3, further comprising a knot formed in said portion of said cord that is embedded in said plug body.

8. The plug of claim 1, further comprising a second tail, said second tail attached to the plug body for use in removing the plug body from the hole.

9. The plug of claim 8, wherein said tail and said second tail are formed from a single cord, a portion of said cord passing through said body of said plug.

10. The plug of claim 1, wherein said plug body is made of a resilient material.

11. The plug of claim 10, wherein said resilient material is silicon.

12. The plug of claim 11, wherein said silicon is an implant grade silicon.

13. A kit for treating osteolysis and other degenerative bone conditions comprising:

a plurality of plugs according to claim 1, a bone regenerative material, a multi-radius bender including a body having first and second ends, a plurality of bending surfaces each having a different radius are disposed at the first end and an aperture sized and configured to receive a shaft of a curette is defined at the second end that is disposed opposite the first end of the multi-radius bender; and an osteolysis brush configured for use in debriding osteolytic material.

14. The kit of claim 13, wherein said tail of each said plug extends from a rim of said trailing end of said plug body adjacent said insertion cavity.

15. The kit of claim 13, further comprising a curette, a cannula configured for use in suctioning osteolytic material out of the osteolytic lesion, a syringe for injecting osteoconductive material into the osteolytic lesion, a syringe loader for transferring the osteoconductive material to the syringe; and a syringe needle.

16. The kit of claim 13, wherein the multi-radius bender includes a handle disposed between the first end and the second end of the multi-radius bender.

17. A plug for plugging a hole of a bone or implant body during injection of an osteoregenerative material, comprising:

a plug body formed from a resilient material, said plug body having a frustoconical configuration narrowing from a trailing end to a leading end for use in plugging a selected hole of the implant body to thereby prevent osteoregenerative material from leaking through the hole, a solid shoulder radially extending from a rim of said trailing end of said plug body, the shoulder being sized and configured to prevent over-insertion of the plug body into the selected hole, a tail, formed from a cord, a distal portion of said cord embedded in said plug body for use in removing the plug body from the hole, said cord extending from said trailing end of said plug body, and said plug body having an insertion cavity inwardly extending from said trailing end in a direction that is parallel to a longitudinal direction of the plug and being sized and configured for use in inserting said plug into a hole of the body, wherein the insertion cavity is disposed adjacent to a location at which the cord is embedded in said plug.

18. The plug of claim 17, wherein said cord is embedded in said plug body substantially along an axis of said plug body and said insertion cavity is formed substantially along said rim of said plug body.

19. The plug of claim 17, wherein said cord is embedded in said plug body substantially along said rim of said plug body and said insertion cavity is formed substantially along an axis of said plug body.

20. The plug of claim 1, wherein said tail extends from a rim of said trailing end of said plug body adjacent said insertion cavity.

21. The plug of claim 1, wherein said tail is integrally molded with said plug body.

* * * * *